United States Patent [19]

Prescott

[11] Patent Number: 5,522,896
[45] Date of Patent: Jun. 4, 1996

[54] BIOCOMPATIBLE COMPOSITE MATERIAL

[75] Inventor: Anthony D. Prescott, Arlington, Tenn.

[73] Assignee: Xomed, Inc., Jacksonville, Fla.

[21] Appl. No.: 222,313

[22] Filed: Apr. 1, 1994

Related U.S. Application Data

[63] Continuation of Ser. No. 9,339, Jan. 26, 1993, abandoned, which is a continuation of Ser. No. 662,361, Feb. 28, 1991, abandoned, which is a continuation of Ser. No. 310,646, Feb. 15, 1989, abandoned.

[51] Int. Cl.$^6$ .................................. A61F 2/28; A61F 2/12
[52] U.S. Cl. ................................... 623/16; 623/8; 623/11
[58] Field of Search .......................... 623/7, 8, 11, 16, 623/17, 18; 433/212.1

[56] References Cited

U.S. PATENT DOCUMENTS

| | | | |
|---|---|---|---|
| 4,131,597 | 12/1978 | Blüethgen et al. | 260/42 |
| 4,349,470 | 9/1982 | Battista | 260/117 |
| 4,386,179 | 5/1983 | Sterling | 524/269 |
| 4,481,323 | 11/1984 | Sterling | 524/269 |
| 4,511,354 | 4/1985 | Sterling | 604/98 |
| 4,548,959 | 10/1985 | Nagai et al. | 523/115 |
| 4,563,486 | 1/1986 | Nemcek et al. | 523/115 |
| 4,613,640 | 9/1986 | Deisler et al. | 524/264 |
| 4,623,553 | 11/1986 | Ries et al. | 427/2 |
| 4,659,617 | 4/1987 | Fujii et al. | 428/221 |
| 4,713,077 | 12/1987 | Small | 623/16 |
| 4,722,948 | 2/1988 | Sanderson | 523/115 |
| 4,776,890 | 10/1988 | Chu | 623/16 X |
| 4,849,285 | 7/1989 | Dillon | 428/330 |
| 4,859,383 | 8/1989 | Dillion | 264/43 |
| 4,863,472 | 9/1989 | Tormala et al. | 623/66 X |
| 4,968,317 | 11/1990 | Tormala et al. | 606/77 |
| 4,976,736 | 12/1990 | White et al. | 623/16 |
| 5,067,965 | 11/1991 | Ersek et al. | 623/11 X |
| 5,074,878 | 12/1991 | Bark et al. | 623/8 |
| 5,084,051 | 1/1992 | Tormala et al. | 623/13 X |
| 5,116,371 | 5/1992 | Christensen et al. | 623/11 |

OTHER PUBLICATIONS

"Biomaterials" by L L Hench, May 23, 1980.

*Primary Examiner*—Debra S. Brittingham
*Attorney, Agent, or Firm*—John S. Hale; Gipple & Hale

[57] ABSTRACT

A non-percutaneous prosthesis, reconstructive sheeting and composite material which exhibit excellent tissue adhesion, outstanding biocompatibility, moldability, trimability and flexibility are disclosed. The non-percutaneous prosthesis, reconstructive sheeting and composite material can be easily molded into various shapes, trimmed with a scalpel and deformed during prosthetic positioning. The non-percutaneous prothesis comprises a biocompatible composite material which is made of an elastomeric material and bio-active ceramic or glass particles and has a predetermined shape. The bio-active ceramic or glass particles are dispersed throughout a matrix of the elastomeric material having a predetermined shape, or the elastomeric material is formed to the predetermined shape and the bio-active ceramic or glass particles are coated on a surface of the elastomeric material. In another embodiment, the non-percutaneous prosthesis comprises a base material of predetermined shape and a layer of elastomeric material provided on the base material, wherein a layer of elastomeric material has distributed therein or provided thereon bio-active ceramic or glass particles. The elastomeric material is preferably one of silicone, polyurethane and its derivatives, hydrogel and C-Flex® and, more preferably, is silicone or hydrogel. The bio-active ceramic or glass particles are preferably made of hydroxylapatite. The reconstructive sheeting comprises a biocompatible composite material made of an elastomeric material and bio-active ceramic or glass particles. Also, the present invention provides a biocompatible composite material comprising hydrogel and particles of a bio-active ceramic or glass material. The particles are preferably dispersed throughout a matrix of hydrogel.

11 Claims, 2 Drawing Sheets

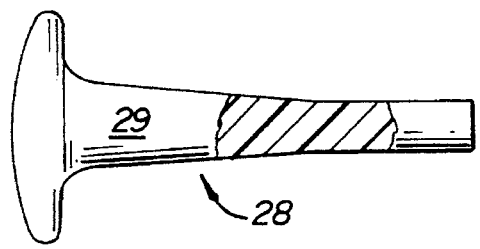
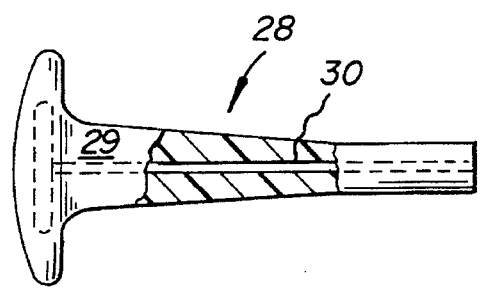
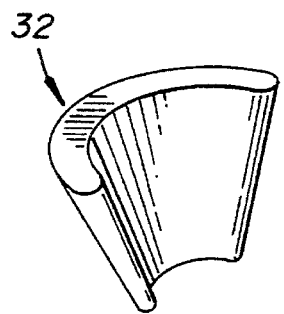
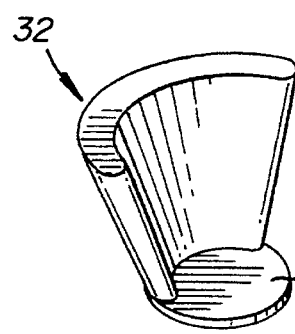
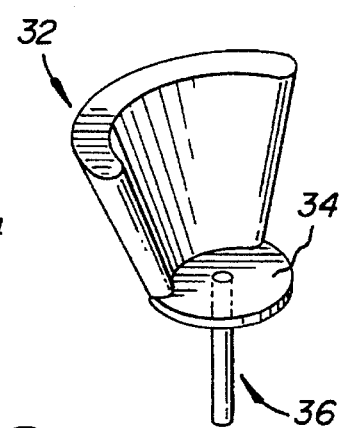
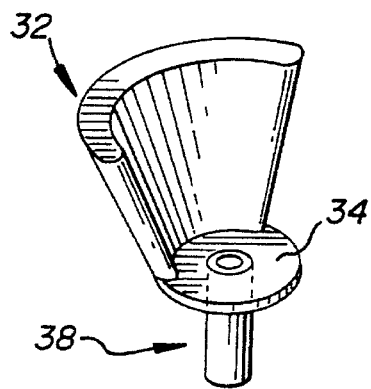
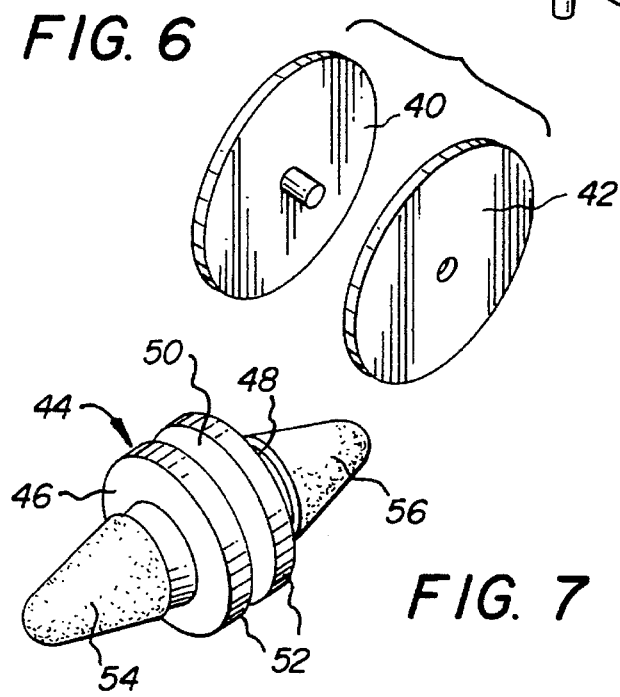

BIOCOMPATIBLE COMPOSITE MATERIAL

RELATED APPLICATION

This application is a continuation of U.S. application Ser. No. 08/009,339 filed Jan. 26, 1993, abandoned, by Anthony D. Prescott and entitled "Biocompatible Composite Material and Prostheses and Method for Using the Same", now abandoned, which is a continuation of U.S. application Ser. No. 07/662,361 filed Feb. 28, 1991, now abandoned, which is a continuation of U.S. application Ser. No. 07/310,646 filed Feb. 15, 1989, now abandoned. This application is also related to United States pending patent application Ser. No. 08/420,436 filed Apr. 10, 1995, which is a continuation of Ser. No. 08/081,089 filed Jun. 21, 1993 (abandoned), and to Ser. No. 08/081,090 filed Jun. 21, 1993 (abandoned).

TECHNICAL FIELD OF THE INVENTION

This invention relates in general to prosthetic implants and, more particularly, to bioactive prosthetic implants.

BACKGROUND OF THE INVENTION

The present invention relates to a biocompatible composite material which exhibits excellent tissue adhesion, outstanding biocompatibility, moldability, trimability and flexibility and to prostheses and reconstructive sheeting comprising such a material.

One material in use for reconstruction of tissue deformities is silicone. Silicone is a soft, pliable material which is easily molded to custom shapes and can be easily deformed during positioning of a prosthesis made therefrom. However, silicone has less than optimum biocompatibility. Moreover, it is difficult to anchor a prosthesis made from silicone due to its poor tissue adhesion. Therefore, silicone prostheses must be fixed by sutures and/or texturing the silicone surface to promote mechanical tissue adhesion.

Hydroxylapatite, on the other hand, exhibits the ability to form a tight bond with surrounding tissues. However, hydroxylapatite is a ceramic material and is, therefore, very brittle and somewhat difficult to form into usable shapes.

U.S. Pat. No. 4,192,021 to Deibig et al discloses bone replacement or prosthesis anchoring material on the basis of sintered calcium phosphates which consists of a mixture of calcium phosphates with low- or high-molecular weight organic substances. More specifically, the anchoring material consists of a mixture of calcium phosphates composed of CaO and $P_2O_5$ in a quantitative ratio of 2:1 to 4:1 with biodegradable polymers in a ration of 10:1 to 1:1 of phosphate to polymer and is implantable as a solid body. A method for the production of the material is disclosed wherein calcium phosphate with a porosity of 15 to 30 volume percent is used and its pores are filled by impregnation with polymer material.

U.S. Pat. No. 4,222,128 to Tomonaga et al discloses a composite implant material comprising a sintered apatite material and a thermoplastic or thermosetting resin. The composite material is prepared by forming a sintered apatite material and filling or impregnating a thermoplastic or thermosetting resin into the pores or holes of the sintered apatite material, which have been formed during the formation of the sintered material or perforated after the formation thereof. However, while this patent discloses the composite implant material to have excellent physical strength, the material cannot be molded or easily trimmed to custom shapes by the physician.

U.S. Pat. No. 4,645,503 to Lin et al discloses a moldable bone-implant material containing between about 65 to 95% hard filler particles and a binder composed of between about 35 to 5% of a biocompatible, biodegradable, thermo-plastic polymer which has fluidic flow properties at or below about 60° C. One preferred binder is polylactic acid having a molecular weight between 400 and 5,000 daltons, and a preferred hard filler is hydroxylapatite. In use, the material is warmed to a temperature which allows molding, and the bone site is filled with the moldable material which then forms a contour-fitting, semi-rigid implant. The implant retains its contour fit and acquires a rigid final state as the binder in the implant is gradually biodegraded and replaced through tissue ingrowth from the surrounding bone site. However, this material is intended to be semi-rigid rather than flexible, and is made to resorb after a period of time rather than remain indefinitely. In addition, the polylactic acid tends to resorb too rapidly, causing inflammation.

U.S. Pat. No. 4,636,526 to Dorman et al discloses composites of unsintered calcium phosphates and synthetic biodegradable polymers useful as hard tissue prosthetics. The composite materials may be ground and blended with a compatible water-soluble pore-forming agent and then molded to form dense, shaped objects which may be made porous by leaching out the water-soluble pore-forming agent. The composites may be used as hard tissue prosthetics either alone or in conjunction with conventional prostheses. The polymers in the composites of the invention of Dorman et al are biocompatible synthetic polymers which are biodegradable.

U.S. Pat. No. 4,610,693 to Niwa et al discloses an implanting article molded by centrifugal dispersion and the method for producing the same. The implanting article includes a base body comprised of a mother material and a surface portion containing dispersed apatite particles. The base body and the surface portion are formed in a mold by solidifying the mother material containing apatite particles under centrifugal force. As the mother material, metals such as aluminum and aluminum alloys and synthetic resin may be employed. As the synthetic resin, phenol resin, polyester resin, urethane resin, epoxy resin, fluororesin, polysulfonic resin, polyethylene resin, polyamide resin, polypropylene resin, polyvinyl chloride resin, polycarbonate resin, polymethyl methacrylic resin, a mixture thereof and a co-polymer composed of two or more of polymerizable monomers can be used.

U.S. Pat. No. 4,693,896 to Vit et al relates to a method of processing sinterable powders into sintered ceramic products and to forms of aluminum oxide, hydroxylapatite, and tricalcium phosphate ceramic products. A preferred dental restorative composition of Vit et al comprises about 5% up to about 90% by weight of hydroxylapatite ceramic dispersed within about 10% to about 95% by weight of an orally compatible binder. Suitable binders include inorganic binders such as a binder comprised of plaster of paris and water. Alternative binding materials include polymeric or polymerizable materials in combination with the appropriate additives for hardening the binder, e.g., cross-linking agents, polymerization catalysts, diluents, etc. The polymeric or polymerizable binder may be selected from a broad group of known polymeric materials suitable for use in the oral cavity. Such materials include, for example, polymethacrylates such as hydroxyethyl methacrylate, polymethyl methacrylate, as well as other polyacrylic acids or esters, epoxy resins, polyesters, etc.

U.S. Pat. No. 4,719,918 to Bonomo et al and U.S. Pat. No. 4,684,370 to Barrett disclose use of hydroxylapatite for alveolar ridge augmentation.

U.S. Pat. No. 4,365,356 to Broemer et al relates to prosthesis parts which are obtained by providing a material as used for prostheses with an enamel or enamel-like coating and incorporating in the enamel layer, while in a viscous state, a bio-active material.

Japanese Laid-Open Patent Publication No. 281954/87 discloses a device having a through-hole therein for permitting communication between the inside and outside of a living body. The substrate of the device is formed of a polymeric material such as polypropylene, silicone rubber, fluorine resin or polyurethane, and a calcium phosphate-type compound and/or a ceramic powder is caused to exist at least on the outside surface of the material which makes contact with biological tissue. However, this document relates to a device for permitting communication between the inside and outside of a living body, i.e., a percutaneous device, and does not relate to a prosthesis or to reconstructive sheeting and, in particular, does not relate to a prosthesis for subcutaneous, middle ear or nasal implantation in a living body.

Therefore, it is still desired to provide a biocompatible composite material suitable for use as a non-percutaneous prosthesis or reconstructive sheeting which exhibits excellent tissue adhesion, outstanding biocompatibility, moldability, trimability and flexibility. It is also desired to provide such a biocompatible composite material, non-percutaneous prostheses and reconstructive sheeting which are non-resorbable.

SUMMARY OF THE INVENTION

The present invention provides a non-percutaneous prosthesis, reconstructive sheeting and a composite material which exhibit excellent tissue adhesion, outstanding biocompatibility, moldability, trimability and flexibility. The non-percutaneous prosthesis, reconstructive sheeting and composite material can be easily molded into various shapes, trimmed with a scalpel and deformed during prosthetic positioning.

The non-percutaneous prothesis comprises a biocompatible composite material having a predetermined shape. The biocompatible composite material is made of an elastomeric material and bio-active ceramic or glass particles. The bio-active ceramic or glass particles are dispersed throughout a matrix of the elastomeric material having a predetermined shape, or the elastomeric material is formed to the predetermined shape and the bio-active ceramic or glass particles are coated on a surface of the elastomeric material.

In another embodiment, the non-percutaneous prosthesis comprises a base material of predetermined shape and a layer of elastomeric material provided on the base material, wherein a layer of elastomeric material has distributed therein or provided thereon bio-active ceramic or glass particles.

The elastomeric material is preferably one of silicone, polyurethane and its derivatives, hydrogel and C-Flex® and, more preferably, is silicone or hydrogel. The bio-active ceramic or glass particles are preferably made of hydroxylapatite.

The reconstructive sheeting comprises a biocompatible composite material made of an elastomeric material and bio-active ceramic or glass particles.

Also, the present invention provides a biocompatible composite material comprising hydrogel and particles of a bio-active ceramic or glass material. The particles are preferably dispersed throughout a matrix of hydrogel.

BRIEF DESCRIPTION OF THE DRAWINGS

FIGS. 4a and 4b are partially cut-away elevational views of total ossicular replacement prostheses in accordance with the present invention;

FIGS. 5a to 5d are perspective views of middle ear prostheses in accordance with the present invention;

FIG. 6 is an exploded perspective view of a nasal prosthesis in accordance with the present invention; and FIG. 7 is a perspective view of a finger joint prosthesis in accordance with the present invention.

DETAILED DESCRIPTION OF THE INVENTION

Figure 1A:
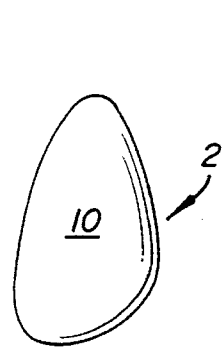
FIGS. 1a to 1c are cross-sectional views of prostheses having a shape useful as breast prostheses in accordance with the present invention.

The protheses of the present invention have predetermined shapes designed for non-percutaneous implantations in a living body. The non-percutaneous prostheses of the present invention include middle ear, nasal and subcutaneous prostheses. The term "subcutaneous" is intended to have its commonly accepted definition, i.e., "located beneath the skin" (in contrast with "percutaneous", i.e., "through the skin"), but is not intended to be limited to meaning immediately beneath the skin. Examples of non-percutaneous protheses according to the present invention include breast prostheses, chin prostheses, fascial prostheses, cleft palate protheses, finger joint protheses, ossicular replacement devices, reconstructive devices for diseased middle ears, protheses to close nasal perforations, etc.

The prosthesis of the present invention comprises a biocompatible composite material having a predetermined shape. The biocompatible composite material is made of an elastomeric material and bio-active ceramic or glass particles. The bio-active ceramic or glass particles can be dispersed through the matrix of the elastomeric material which has the predetermined shape. Alternatively, the elastomeric material having he predetermined shape may have the bio-active ceramic or glass particles coated on its surface by any known method, such as spraying using a compressed gas propellant.

The elastomeric material is preferably silicone. However, other materials such as polyurethane and its derivatives, hydrogels such as polyvinyl pyrrolidone and its derivatives and polyhema, C-Flex®, etc., may be used. The elastomeric material may be in the form of an open-or closed-cell foam.

C-Flex® is a thermoplastic elastomer manufactured by Concept Polymer Technologies, Inc., of Clearwater, Fla., and is formulated from a styrene-ethylene-butylene-styrene (SEBS) modified polymer.

The bio-active particulate material forms a chemical attachment with the surrounding tissue. Any bio-active ceramic or bio-active glass particulate material which is biocompatible and forms a chemical attachment with the surrounding tissue may be used. However, calcium phosphates, especially hydroxylapatite, are preferred. Silica-based glasses such as Ceravital® (available from Ernst Leitz Wetzlar GmbH of West Germany), BioGlass® (available from the University of Florida in Gainesville), etc., may also be used. The particles preferably have a particle size in the range of 2 to 500 microns.

The proportion of bio-active ceramic or glass particles and elastomeric material used in the prosthetic device of the present invention varies depending upon the intended end use. In general, however, with respect to the prosthetic device of the present invention wherein the bio-active ceramic or glass particles are dispersed throughout a matrix of elastomeric material, the bio-active ceramic or glass particles are preferably contained in the matrix in an amount of 20 to 70 weight % based on the total amount of bio-active ceramic or glass particles and elastomeric material. Above 70 weight %, the strength of the composite decreases.

The elastomeric matrix may be an open-cell foam material, such as polyurethane open-cell foam. Bioactive ceramic or glass particles, such as hydroxylapatite, can be dispersed throughout the open-cell foam matrix. Such a composite would be more elastic than its non-foam counter-part. Also, such a composite would invite tissue ingrowth.

When the bio-active ceramic or glass particles are coated on the surface of an elastomeric material having a predetermined shape, the amount of bio-active ceramic or glass particles is such that nearly the entire exposed surface is coated with hydroxylapatite so as to increase tissue adhesion. However, if desired, exposure may be reduced to decease tissue adhesion. The elastomeric material can be substantially coated with larger sized particles and finer particles may be used to fill spaces between the larger particles.

The prothesis of the present invention can also comprise a base material of predetermined shape, e.g., a conventional prosthetic device, and a layer of elastomeric material provided on the base material, wherein the layer of elastomeric material has distributed therein or provided thereon bio-active ceramic or glass particles.

The elastomeric materials and bio-active ceramic or glass particles previously described are also useful in this embodiment. The elastomeric material in this embodiment may be in the form of a closed-cell foam material which would be more elastic than its non-foam counterpart.

Protheses of various shapes are shown in FIGS. 1 through 6.

Figure 1B:
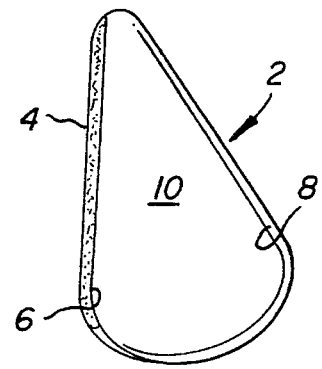
Figure 1C:
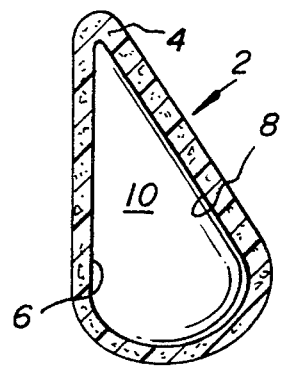

FIGS. 1a to 1c are side cross-sectional views of a prosthesis 2 having a shape useful as a breast prothesis. The prosthesis shown in FIG. 1a comprises a biocompatible composite material wherein bio-active ceramic or glass particles are dispersed through a matrix of elastomeric material. The breast prosthesis 2 shown in FIG. 1b has a coating 4 on its proximal side 6. FIG. 1c shows a breast prosthesis 2 having a coating 4 covering the entire surface thereof including the proximal side 6 and distal side 8. The breast prosthesis 2 shown in FIG. 1a or 1b has a base material 10 which may be the same material as that used in the prosthesis shown in FIG. 1a or may be a conventional prosthesis such as a conventional silicone breast prosthesis. The coating 4 can comprise an elastomeric material having distributed therein or provided thereon bio-active ceramic or glass particles.

Figure 2A:
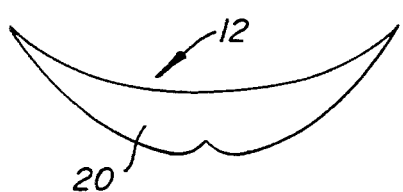
FIGS. 2a to 2d are cross-sectional plan views of prostheses having a shape useful for a chin implant in accordance with the present invention.
Figure 2B:
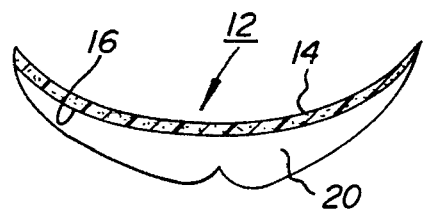
Figure 2C:
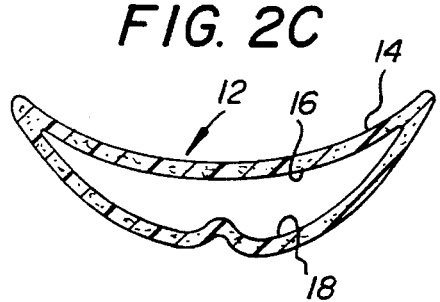
Figure 2D:
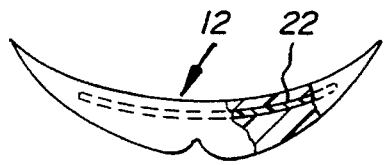

FIGS. 2a through 2d are cross-sectional plan views of a prosthesis 12 having a shape such that it is useful as a chin implant. FIG. 2a shows a prosthesis 12 made of a composite material wherein bio-active ceramic or glass particles are dispersed throughout a matrix of elastomeric material. FIG. 2b shows a prosthesis 12 having a coating 14 covering the proximal side 16 of the prosthesis 12. FIG. 2c shows a coating 14 covering the entire surface of the prosthesis 12 including the proximal side 16 and distal side 18. The base material 20 of the protheses shown in FIGS. 2b or 2c can be the same composite material as used in the prosthesis 12 shown in FIG. 2a or can be a conventional material such as silicone. The coating 14 comprises an elastomeric material having distributed therein or provided thereon bio-active ceramic or glass particles. FIG. 2d shows a prosthesis 12 having a malleable metal strip or mesh 22 therein to aid in maintaining a desired shape. The strip or mesh 22 may also be used in the coated protheses 12 shown in FIGS. 2b and 2c.

Figure 3A:
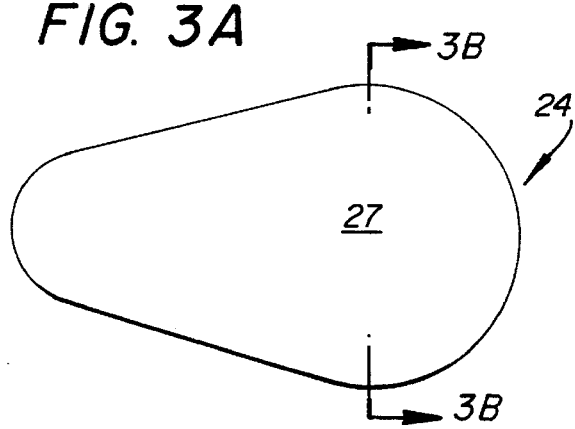
FIG. 3a is a top cross-sectional view of an implant having a shape useful as a cheek augmentation device in accordance with the present invention.
Figure 3B:
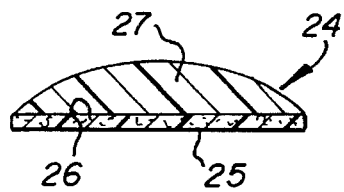
FIG. 3b is a side cross-sectional view of the implant shown in FIG. 3a along line 3B—3B.

FIGS. 3a and 3b are top and side cross-sectional views of an implant 24 having a shape such that it is useful as a cheek augmentation device. The prosthesis 24 can be made of the material 27 such as that described above with reference to the breast prosthesis 2 and chin implant 12 and can be coated with bio-active particles 25 either on its proximal side 26 or on its entire surface as described above with respect to the breast prosthesis 2 and chin implant 12.

FIG. 4a is a partially cut-away elevational view of a prosthesis 28 having a shape such that it is useful as a total ossicular replacement device similar to that described in U.S. Pat. No. 4,510,627 to Treace. The prosthesis 28 can be made of a material 29 such as that described in connection with the prostheses 2, 12, and 24 shown in FIGS. 1a, 2a, and 3, respectively. The prosthesis 28 shown in FIG. 4b has a malleable metal strip or mesh 30 to aid in forming or maintaining a desired shape.

FIG. 5a shows a prosthesis 32 having a shape such that it is useful to reconstruct a canal wall of diseased middle ear. The prosthesis shown in FIG. 5b has a canal wall section 32 and tympanic membrane replacement section 34. FIG. 5c shows a prosthesis having a canal wall section 32, tympanic membrane 34 and total ossicular replacement portion 36. FIG. 5d shows a prosthesis having a canal wall section 32, tympanic membrane section 34 and partial ossicular replacement portion 38. The canal wall portion 32 may have incorporated therein a malleable metal strip or mesh to aid in maintaining the desired shape. The prosthesis shown in FIG. 5c may have a wire in the shaft to aid in its positioning the prostheses shown in FIGS. 5a through 5d may be made from the materials previously described.

FIG. 6 is an exploded perspective view of a set of disks 40 and 42 having a shape useful to close nasal perforations.

FIG. 7 is a perspective view of a finger joint prosthesis 44 according to the present invention. Such a prosthesis is formed of a base material 46 which is preferably silicone. The base material 46 has a coating 48 of bio-active particles, preferably hydroxylapatite particles, at each of its generally cone-shaped ends 54 and 56. The finger joint 44 has two generally annular flanges 52 and a narrowed hinge section 50 between the flanges 52. The cone-shaped ends 54 and 56 are placed within a pair of finger bones and are joined thereto with a build-up of fibrous tissue. The hinge 50 acts as an artificial knuckle.

The prostheses of the present invention can also have shapes such that they are useful as cleft palate prostheses, reconstructive sheeting, wire mesh or polymer fiber mesh reinforced reconstructive sheeting, etc.

The reconstructive sheeting of the present invention is designed for reconstruction of tissue of a living body and comprises a biocompatible composite material made of bio-active ceramic or glass particles dispersed through a sheet of elastomeric material. The sheet may have a wire mesh or polymer fiber mesh reinforcement therein. The reconstructive sheeting may be molded to form prosthetic devices for repair or replacement of, e.g., the trachea, soft tissue defects, orbital floor and cranial perforations, or to fix or hold other prosthesis in place. The sheeting may also be used as artificial skin. The sheeting is preferably formed to have a thickness in the range of 0.005 to 0.1 inches.

An extremely useful biocompatible composite material according to the present invention comprises hydrogel and particles of a bio-active ceramic or glass material. The particles of bio-active ceramic or glass material are preferably dispersed throughout a matrix of the hydrogel. For example, a composite consisting essentially of polyvinyl pyrrolidone hydrogel and hydroxylapatite is rigid when dry, but softens when exposed to moisture. This property could be used to form a cutting edge which would soften into a feathered edge when implanted.

This composite material can be provided to the physician previously molded, whereby the physician could trim or deform the molded composite material before or during positioning. In addition, this composite material can be provided to the physician uncured, molded by the physician and subsequently cured either at room temperature or by addition of a catalyst, etc.

The following experiments were conducted to study the properties and feasibility of use of various biocompatible composite materials.

Experiment 1

Materials:
Dow Corning heat-curable MDX4-4516 silicone lot A rubber and>200 mesh size hydroxylapatite particles. Silicone weight–3.3 grams.

Using a rolling pin, the silicone was flattened to a thickness of approximately 1/16 inch. The hydroxylapatite particles were then poured out onto a flat surface. The silicon sheet was then placed over the hydroxylapatite particles. The rolling pin was used to force the hydroxylapatite particles into the silicone matrix. The silicone/hydroxylapatite composite was then folded onto itself and the entire process was repeated until the composite began to separate when folded.

Maximum final weight=6.8 mg.
Hydroxylapatite weight=6.8–3.3=3.5 mg=51.5 wt. %
The composite was then placed in an oven and cured.
Results:
The material appeared very firm and tough after it was cured. Blending of the hydroxylapatite particles appeared uniform. Better blending techniques could be used such as introducing both materials into the barrel of an injection molding machine and allowing the screw to blend the components. The silicone used in Experiment 1 is a high durometer material and would be suitable for fabricating stiff sheeting or prostheses where rigidity is important.

Experiment 2

Materials:
Dow Corning MDX4-4516 silicone rubber and through 300 mesh hydroxylapatite powder.
Silicone weight=3.65 grams
The steps described in Experiment 1 were repeated.
Maximum final weight=5.5 grams
Hydroxylapatite weight=5.5–3.65=1.85 grams=33.6 wt. %
Results:
Particle size of the hydroxylapatite is much smaller than in Experiment 1. The material did not seem to stick together as well (i.e., did not form a cohesive mass) when blending. Upon examination after final curing, the composite was made of very thin, fine, tough sheets of silicone/hydroxylapatite. This material could be ideal for tympanic membrane reconstruction or soft tissue repair.

Experiment 3

Materials:
Dow Corning silicone rubber Q7-4635, heat-cured and<300 mesh hydroxylapatite powder. Silicone weight=2.6 grams
The steps described in Experiment 1 were repeated.
Final weight=3.5 grams
Hydroxylapatite weight=3.5–2.6=0.9 grams=25.7 wt. %
Results:
The results were similar to those obtained in Experiment 2, but since a lower durometer silicone was used, the composite was more pliable.

Experiment 4

Materials:
Dow Corning silicone rubber Q7-4635 and hydroxylapatite powder>200 mesh.
Silicone weight=2.4 grams
The steps described in Experiment 1 were repeated.
Final weight–5.0 grams
Hydroxylapatite weight=5.0–2.4=2.6 grams=52 wt. %
Results:
The results were similar to those obtained in Experiment 1, but since a lower durometer silicone was used, the composite was more pliable.

Experiment 5

Materials:
Dow Corning Silicone MDX4-4210 RTV 2 parts (A+B) silicone Lot #HH068476 and hydroxylapatite powder>200 mesh.
Container weight=0.65 gram
Container+part A=6.0 grams
Container+part A+part B=6.7 grams
Silicone weight=6.05 grams
Container+part A+part B+hydroxylapatite=11.2 grams
Hydroxylapatite weight=4.5 grams=42.7 wt. %
After mixing the hydroxylapatite into the silicone with a stirring rod, additional powder was sprinkled on the surface of the composite to form a hydroxylapatite-enriched surface.
Results:
See Experiment 6 below.

Experiment 6

Materials:
Dow Corning silicone MDX4-4210 and hydroxylapatite powder<300 mesh.
Container weight=0.3 gram
Container+Part A=5.3 gram
Container+Part A+part B=6.1 grams
Container+part A+part B+hydroxylapatite=14.55 grams Hydroxylapatite weight=8.45 grams=59.3 wt. %

Note:

The fine powder appeared to wet quite well. It is possible that hydroxylapatite weight % using this fine powder size could go as high as 70% by weight hydroxylapatite.

Results:

As expected, the composite in Experiment 5 was more grainy or coarse than in Experiment 6. Either of these two materials would be good for casting custom prostheses. These two compositions were sliced in half after curing. The interiors were porous due to the entrapment of air bubbles. These bubbles could be removed by applying a vacuum to the composite and then releasing it prior to curing. On the other hand, additional air bubbles could be incorporated into the composite to form a flexible hydroxylapatite/silicone composite foam. Air bubbles could be incorporated by mechanical agitation or mixing with hydrogen peroxide.

The surface of these composites may not be as bio-active as the interiors due to complete encapsulation of the hydroxylapatite particles by the silicone elastomer. This problem could be avoided by sprinkling hydroxylapatite particles onto the surface of the composite, as in Experiment 5, prior to curing. Another method would be to abrade or roughen the surface after curing to expose hydroxylapatite particles.

All of the materials obtained in Experiments 1 through 6 could be extruded into tubing or custom shapes, if desired.

Experiment 7

Materials:

Silicone/silicone gel breast prosthesis purchased from Surgical Dimensions, Inc., Lilburn, Ga.; Dow Corning RTV silicone adhesive; <300 mesh hydroxylapatite particles; >200 mesh hydroxylapatite particles.

The silicone adhesive was coated onto the medial wall (chest side) of the breast prosthesis. The >200 mesh hydroxylapatite was spread onto a flat surface. The adhesive-coated surface was pressed onto the hydroxylapatite particles, and the <300 mesh hydroxylapatite particles were sprinkled onto the coated surface to fill in the voids between the larger hydroxylapatite particles.

Results:

After curing, the hydroxylapatite particles appeared to be very adherent to the surface of the silicone breast prosthesis. This appears to impart biological fixation and improved biocompatibility to substrate materials. Other substrate materials would include, but not necessarily be limited to, silicones, polyurethanes, and TPR rubber such as C-Flex2®.

The silicone adhesive in Experiment 7 could be blended with particulate hydroxylapatite and put into a tube. A physician could then squeeze the composite out of the tube in the same manner as toothpaste and form custom shapes at the time of surgery.

Experiment 8

Materials:

A material which contains polyvinyl pyrrolidone (marketed under the name Sea Slide by Hydromer, Inc.), and hydroxylapatite particles>200 mesh.

Container weight=0.7 grams

Container+Sea Slide=5 grams

Container+Sea Slide+hydroxylapatite=10.9 grams

Hydroxylapatite weight=5.9 grams=93.7 wt. %

Weight after curing=7.5 grams

The liquid Sea Slide was poured into a 2" diameter container. Hydroxylapatite powder was then added to the liquid until the powder no longer appeared to be wetted by the Sea Slide. The container and contents were then set aside to cure. When removed from the container, the composite fell apart except for a thin skin which formed on the surface of the container. The weight of the container and hydroxylapatite powder minus the skin=5.8 grams.

Results:

As discussed previously, a thin skin of a hydrogel/hydroxylapatite composite formed on the surface. This skin was approximately 47% by weight hydroxylapatite. The skin formed was brittle and grainy until wetted. After wetting with water, the skin became very flexible, but fell apart easily.

Experiment 9

Materials:

Sea Slide and hydroxylapatite powder<300 mesh.

Container weight=0.3 gram

Container+Sea Slide=4.5 grams

Container+Sea Slide+hydroxylapatite=10.55 grams

Hydroxylapatite weight=6.05 grams=86.4 wt. %

Weight after curing=7.3 grams

The steps described in Experiment 8 were repeated. A thick, creamy paste is formed when mixing. Higher weight percentages of hydroxylapatite can be obtained by thinning Sea Slide with water to obtain greater volume and wettability.

Results:

When the finer powder was used, the maximum weight % hydroxylapatite increased. The composite also appeared more durable after wetting than the composite in Experiment 8. The weight % of hydroxylapatite=86.4%.

Experiment 10

Materials:

Sea Slide and hydroxylapatite powder<300 mesh.

Container weight=0.5 gram

Container+Sea Slide=5.1 grams

Container+Sea Slide+hydroxylapatite=6.2 grams

Hydroxylapatite weight=1.1 gram–68.8 wt. %

Weight after curing=2.4 grams

Results:

The weight % hydroxylapatite was reduced in this experiment to 68.8%. The hydroxylapatite particles size was <300 mesh. This material had much better handling characteristics and appeared tougher when wetted than that obtained in either Experiment 8 or Experiment 9.

Experiment 11

Materials:

Sea Slide and hydroxylapatite powder<300 mesh.

Container weight=0.6 gram

Container+Sea Slide=5.3 grams

Container+Sea Slide+Hydroxylapatite=7.8 grams

Hydroxylapatite weight=2.5 grams=71.4 wt. %

Weight after curing=4.1 grams

Results:

The weight % hydroxylapatite was increased to 71.4%. Again, the <300 mesh material was used. This composite also exhibited good handling characteristics when wetted, but was less flexible than that obtained in Experiment 10.

Note:

Experiments 8–11 incorporated only one type of poly vinyl pyrrolidone; other variations of this material may be more appropriate for the intended application of biocompatible composites. Other hydrogels such as those used in contact lenses may also be appropriate, i.e., polyhema.

Experiment 12

To demonstrate calcium ion ($Ca^{2+}$) release, silicone and hydroxylapatite composite sheets and ultraviolet-curable polyurethane and hydroxylapatite composite sheets 0.040 inch thick×1.5 inches×3.0 inches and containing 40% by weight hydroxylapatite were fabricated. Fifty mg. of each material were then suspended in 50 ml of 0.1M potassium acetate buffer, pH 5, for one hour. The buffer was then analyzed for $Ca^{2+}$ content by atomic absorption spectroscopy (AAS). The results, shown in Table 1, indicate that the rate of release of $Ca^{2+}$ ions into the body may be controlled by varying the hydroxylapatite particle size and/or the composition of the substrate material. The rate of $Ca^{2+}$ release may, in turn, effect tissue adhesion.

TABLE 1

| Substrate Material (ppm) | Hydroxylapatite | |
|---|---|---|
| | Particle Size | $Ca^{2+}$ |
| Silicone | between 60 and 200 mesh | 0.510 |
| Silicone | <300 mesh | 0.680 |
| Polyurethane | <300 mesh | 1.548 |

While I have shown and described several embodiments in accordance with the present invention, it is understood that the same is not limited thereto, but is susceptible of numerous changes and modifications as known to a person having ordinary skill in the art, and I therefor do not wish to be limited to the details shown and described herein, but intend to cover all such modifications as are encompassed by the scope of the appended claims.

What is claimed is:

1. A non-porous, non-resorbable synthetic flexible prosthesis for replacement of a soft tissue structure, said prosthesis adapted for connection to soft tissue in the human body, said prosthesis consisting of:

an elastomeric synthetic hydrogel matrix;

a plurality of hydroxylapatite particles distributed throughout said matrix with said hydroxylapatite particles less than 87% by weight and more than 40% by weight of said matrix; and said matrix cured to form said flexible prosthesis such that an applied force can distort said flexible prosthesis and said flexible prosthesis will substantially return to its original shape after said force is removed.

2. A non-porous, non-resorbable prosthesis according to claim 1, wherein said particles have a particle size in the range of 2 to 500 microns and comprise less than 72% by weight of said matrix.

3. A non-resorbable flexible prosthesis having a shape, comprising:

a matrix of a non-resorbable synthetic hydrogel;

a plurality of bioceramic particles dispersed throughout said matrix with said bioceramic particles less than 87% by weight and more than 25% by weight of said matrix; and wherein said matrix is cured such that an applied force can distort said prosthesis from said shape, and said prosthesis will substantially return to said shape after said force is removed.

4. A non-resorbable prosthesis according to claim 3, wherein said bioceramic particles have a particle size in the range of 2 to 500 microns and comprise more than 40% weight of said matrix.

5. A non-resorbable prosthesis according to claim 3, wherein said bioceramic particles comprise hydroxylapatite.

6. A non-resorbable prosthesis according to claim 3, wherein said prosthesis has a shape adaptable to augment or replace a human breast.

7. A non-resorbable prosthesis according to claim 3, wherein said prosthesis has a shape adaptable to augment or replace a human chin.

8. The prosthesis of claim 3, wherein said non-resorbable synthetic hydrogel comprises a polyvinyl pyrrolidone hydrogel.

9. The prosthesis of claim 3 wherein said bioceramic particles comprise hydroxylapatite.

10. A non-resorbable flexible prosthesis comprising:

a matrix of an elastomeric material selected from the group consisting of polyhema, styrene-ethylene-butylene-syrene (SEBS) modified polymer, and silicone; and a plurality of bioceramic particles dispersed throughout said matrix with said bioceramic particles less than 87% by weight and more than 25% by weight of said matrix, wherein said matrix is cured to form said flexible prosthesis such that an applied force can distort said flexible prosthesis from its original shape and said flexible prosthesis will substantially return to said original shape when said force is removed.

11. The prosthesis of claim 10 wherein said bioceramic particles comprise hydroxylapatite.

* * * * *